(12) United States Patent
Kitayama

(10) Patent No.: US 9,265,972 B2
(45) Date of Patent: Feb. 23, 2016

(54) ULTRASONIC TREATMENT DEVICE

(71) Applicant: OLYMPUS CORPORATION, Tokyo (JP)

(72) Inventor: Tadashi Kitayama, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 127 days.

(21) Appl. No.: 14/031,747

(22) Filed: Sep. 19, 2013

(65) Prior Publication Data

US 2014/0088464 A1 Mar. 27, 2014

Related U.S. Application Data

(60) Provisional application No. 61/704,892, filed on Sep. 24, 2012.

(51) Int. Cl.
*A61N 7/00* (2006.01)
*A61B 17/32* (2006.01)

(52) U.S. Cl.
CPC .......... *A61N 7/00* (2013.01); *A61B 17/320092* (2013.01)

(58) Field of Classification Search
CPC .................. A61B 1/00103; A61B 2019/4873; A61B 17/320092; A61N 7/00
See application file for complete search history.

(56) References Cited

U.S. PATENT DOCUMENTS

2005/0033337 A1* 2/2005 Muir et al. .................... 606/167
2013/0046337 A1* 2/2013 Evans et al. .................. 606/205

FOREIGN PATENT DOCUMENTS

| JP | A-7-95982 | 4/1995 |
| JP | A-2000-107189 | 4/2000 |

* cited by examiner

*Primary Examiner* — Michael Rozanski
(74) *Attorney, Agent, or Firm* — Oliff PLC

(57) ABSTRACT

An ultrasonic treatment system includes a probe which transmits ultrasonic vibration. In the system, a first energy generator generates treatment energy suitable for treating a living tissue in accordance with an instruction from a first instruction part. The probe is made ultrasonically vibrate with the first amplitude. A second energy generator generates destruction energy suitable for destroying the probe in accordance with an instruction from a second instruction part. The probe is made ultrasonically vibrate with the second amplitude.

3 Claims, 4 Drawing Sheets

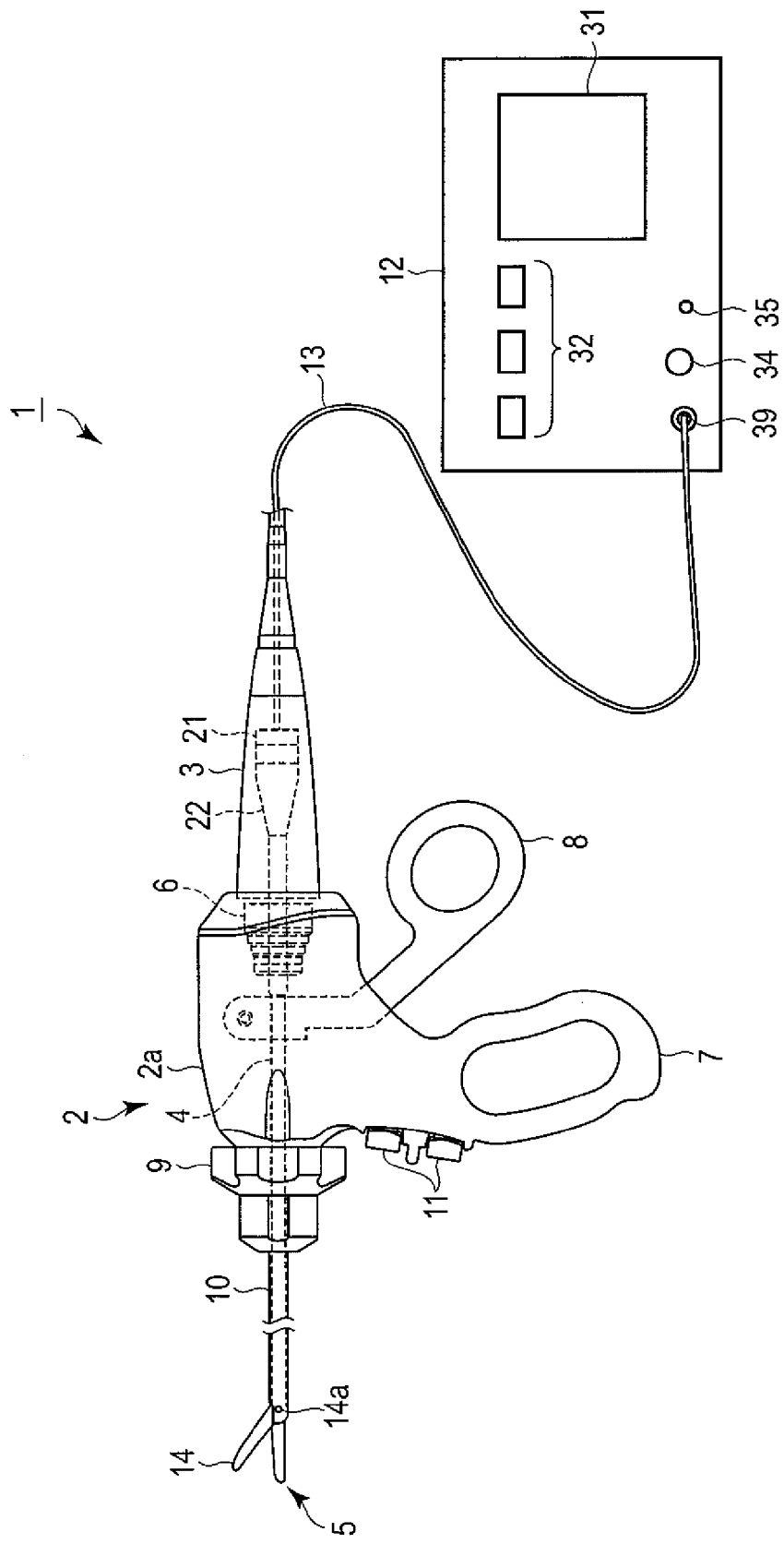
F I G. 1A

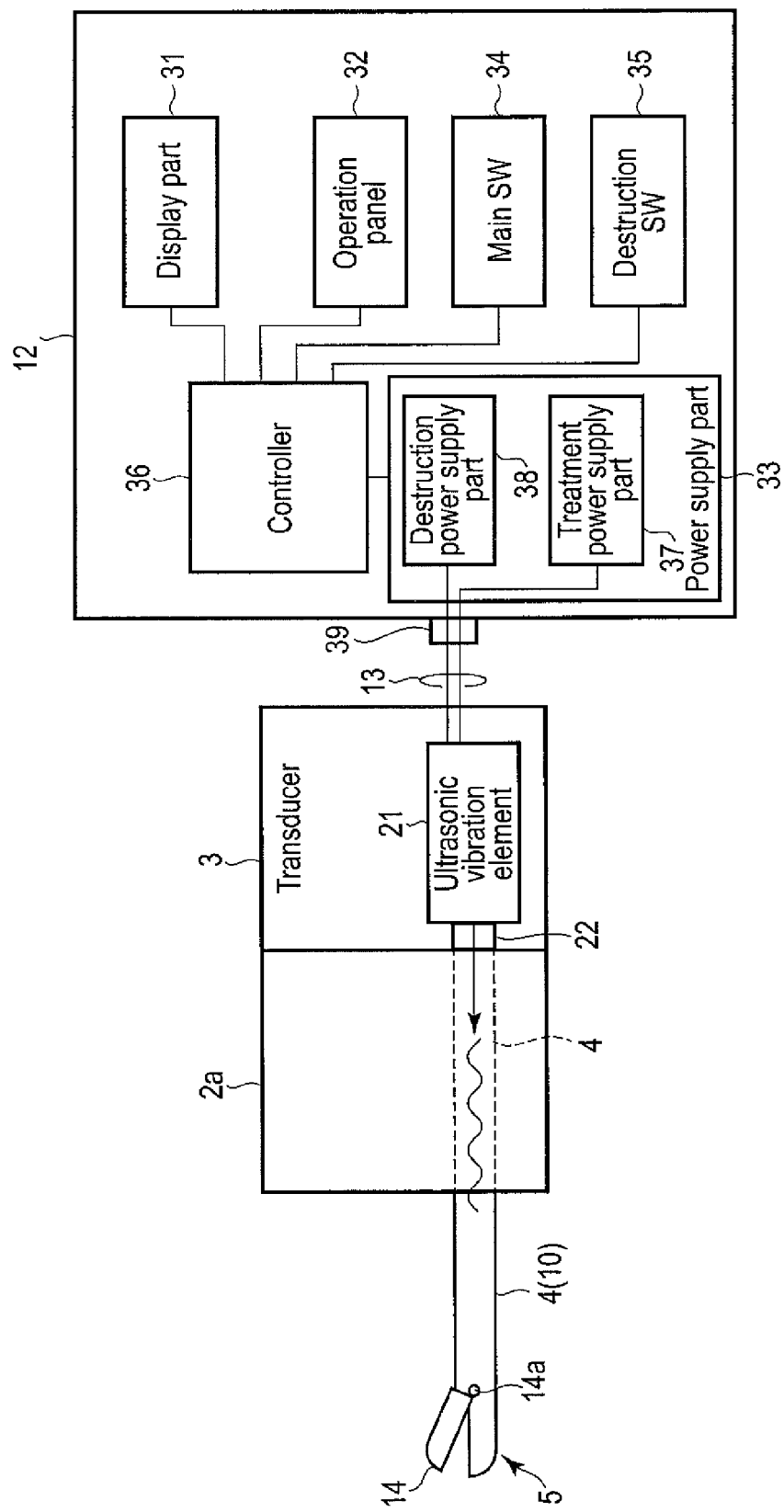
F I G. 1B

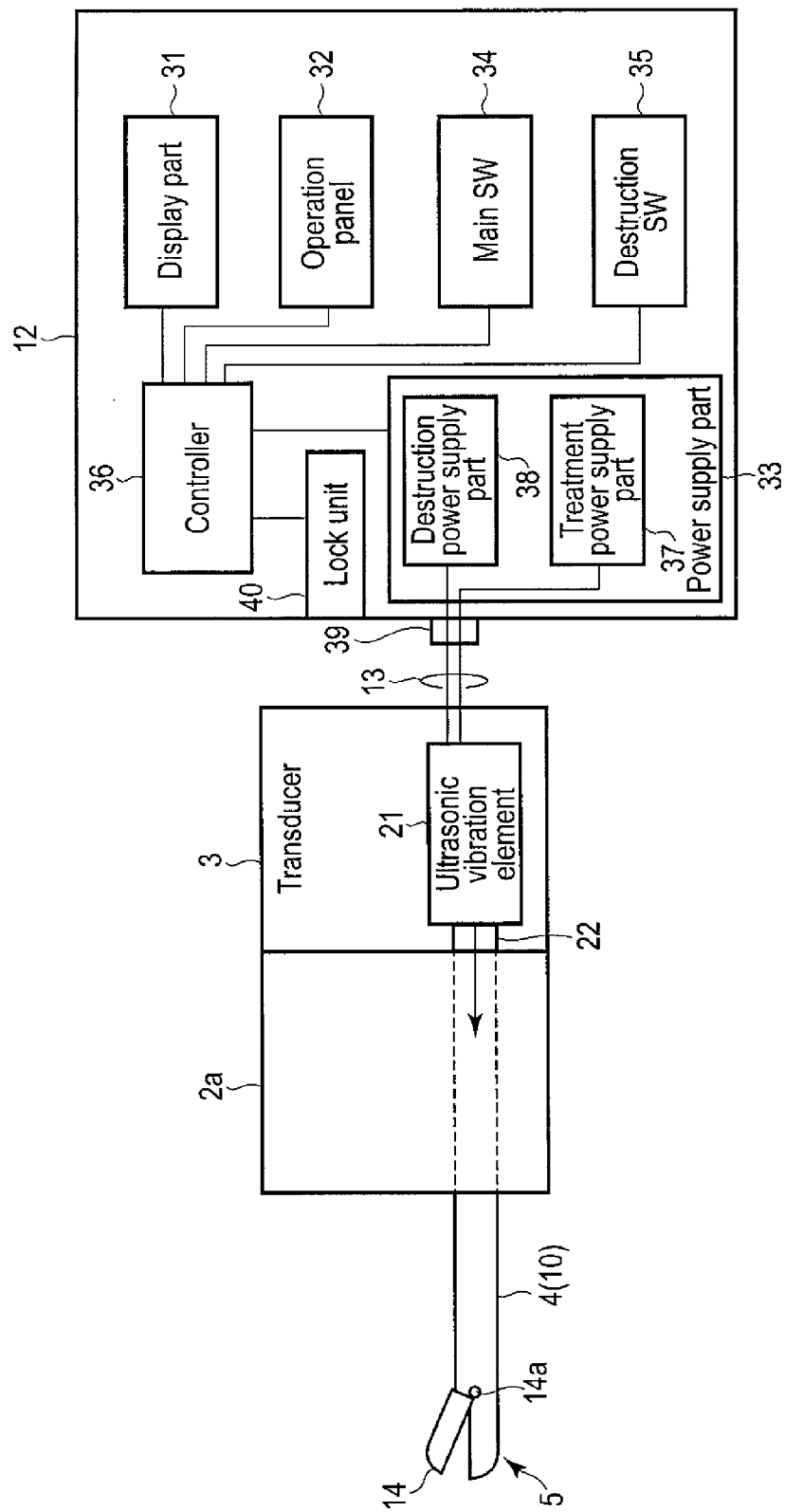
F I G. 4

ULTRASONIC TREATMENT DEVICE

CROSS-REFERENCE TO RELATED APPLICATIONS

This application is based upon and claims the benefit of priority from the prior U.S. Provisional Application No. 61/704,892, filed Sep. 24, 2012, the entire contents of which are incorporated herein by reference.

BACKGROUND OF THE INVENTION

1. Field of the Invention

The invention relates to an ultrasonic treatment system which treats a living tissue by using ultrasonic vibration.

2. Description of the Related Art

There is a disposable treatment instrument among treatment instruments which supply energy, such as ultrasonic vibration or a high-frequency current, to a portion (living tissue) of a target to treat. Such a disposable treatment instrument needs to prevent from being reused from a viewpoint of infection prevention or from a viewpoint of performance as a treatment instrument.

Hence, for example, Jpn. Pat. Appln. KOKAI Publication No. 2000-107189 proposes a treatment instrument in which an electromotive force decreases to be so low that reuse is impossible after being used for a preset time equivalent to duration of one treatment of medical care. In addition, Jpn. Pat. Appln. KOKAI Publication No. 7-095982 proposes a treatment instrument in which a member of a part of a probe is formed of a material containing hydrophilic polymer. At the time of cleaning for sterilization, the treatment instrument is deformed by dissolution or softening thereby to prevent reuse.

BRIEF SUMMARY OF THE INVENTION

According to an embodiment of the present invention, there is provided an ultrasonic treatment system comprising: a transducer unit comprising an ultrasonic transducer which generates ultrasonic vibration; a handle unit comprising a probe which transmits the ultrasonic vibration generated by the transducer unit; a first energy generator which generates treatment energy to ultrasonically vibrate the probe with a first amplitude suitable for a treatment, in order to treat a living tissue; a second energy generator which generates destruction energy to ultrasonically vibrate the probe with a second amplitude suitable for destruction and greater than the first amplitude, in order to destroy the probe; a first instruction part by which an instruction is given to supply the transducer unit with the treatment energy generated by the first energy generator; and a second instruction part by which an instruction is given to supply the transducer unit with the destruction energy generated by the second energy generator.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A conceptually shows a whole ultrasonic treatment system according to the first embodiment;

FIG. 1B is a block diagram showing a configuration of an ultrasonic treatment system according to the first embodiment;

FIG. 4 is a block diagram showing a configuration of an ultrasonic treatment system according to a modification of the first embodiment.

BRIEF DESCRIPTION OF THE PREFERRED EMBODIMENT

Figure 2:
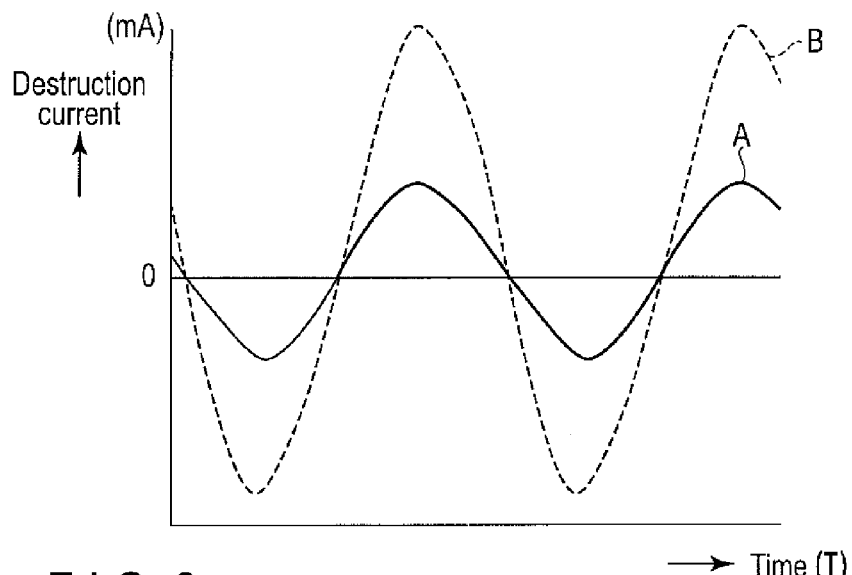
FIG. 2 shows a waveform of a treatment current generated by a first energy generator, and a waveform of a treatment current generated by a second energy generator, according to the first embodiment.

Hereinafter, embodiments of the invention will be described in details with reference to the drawings.

First Embodiment

FIG. 1A conceptually shows a whole ultrasonic treatment system according to the first embodiment. FIG. 1B is a schematic block diagram showing a configuration of the ultrasonic treatment system.

The ultrasonic treatment system 1 according to the present embodiment performs treatments such as incision and solidification by ultrasonic vibration. In descriptions below, a side where a treatment part 5 described later exists is supposed to be the front (or a tip side), and another side where a transducer unit 3 is supposed to be the rear (or a base-end side).

The ultrasonic treatment system 1 is configured by: a handle unit 2 comprising a treatment part which performs a treatment on a living tissue by ultrasonic vibration; the transducer unit 3 which generates ultrasonic vibration; and a power supply unit 12 which supplies drive energy to the transducer unit 3. The handle unit 2 and the transducer unit 3 form a treatment instrument.

In the present embodiment, body exterior of the handle unit 2 is formed of a resin material in a pistol shape, and a treatment instrument 5 is integrally provided in direct contact with a portion as a treatment target. Since an operator grasps a handle in a hand, the handle unit 2 is configured to be disposable without being subject to reuse in consideration of hygiene and safety. The transducer unit 3 does not directly touch any treatment target portion, and is therefore reused repeatedly after being subject to cleaning and a sterilization treatment. Needless to say, the transducer unit 3 needs not be reused but may be also disposable.

The transducer unit 3 is connected to the power supply unit 12 through a power supply cable 13. The transducer unit 3 has a well-known configuration which contains an ultrasonic vibration element (for example, a piezoelectric element) 21 and a horn part 22 in a casing. The ultrasonic vibration element 21 is connected to the power supply unit 12 through the power supply cable 13 by an unillustrated internal wiring, and is supplied with drive energy. Accordingly, the ultrasonic vibration element 21 ultrasonically vibrates. The horn part 22 increases an amplitude of ultrasonic vibration generated by the ultrasonic vibration element 21. The power supply cable 13 is detachable from and attachable to the power supply unit 12 through the connector 39.

The handle unit 2 comprises a unit body 2, a transducer attachment part 6, a fixed handle 7, a movable handle 8, a rotary knob 9, a probe 4, a sheath 10, and a switch 11.

The probe 4 comprises a tip end part and a base-end part, and is configured by a rod-like member extending in a longitudinal axial direction. The base-end part of the probe 4 is connected to the horn part 22 of the transducer unit 3 inside the unit body 2. The base-end part of the probe 4 is jointed to the horn part 22 (i.e., the transducer unit 3), tightened to a setting value which is set in advance by a torque wrench. By connecting (fixing) with the torque wrench, the probe 4 and the horn part 22 of the transducer unit 3 are brought into tight contact with each other in a proper contact state (a connected state). In this manner, ultrasonic vibration generated by the transducer unit 3 is excellently transmitted to the tip end part from the base-end part of the probe 4. Further, the treatment part 5 which treats a living tissue is formed at the tip end part of the probe 4. The treatment part 5 makes contact with a living tissue and performs a treatment by transmitted ultrasonic vibration. Thus, the probe 4 is connected to the transducer unit 3 inside the unit body 2, and propagates ultrasonic vibration to the treatment part 5 formed at the tip end part. The probe 4 has a size which makes at least the treatment part 5 exposed to outside of the exterior of the unit body 2 when the probe 4 is connected to the transducer unit 3.

The sheath 10 covers the probe 4 extended to outside of the unit body 2. Specifically, the sheath 10 covers the other part of the probe 4 extended to outside of the unit body 2 than the treatment part 5. In this manner, the treatment part 5 is not covered with the sheath 10 but is exposed outside.

A jaw 14 is provided in front of (or at a tip end of) the sheath 10. The jaw 14 is can open/close in relation to the treatment part 5 through a pivot support part 14a. By closing the jaw 14, a living tissue can be grasped between the jaw 14 and the treatment part 5.

The transducer attachment part 6 is provided behind (at the base-end of) the unit body 2, and the rotary knob 9 is provided in front of (at the tip end) of the unit body 2.

The transducer attachment part 6 is provided in order to attach the transducer unit 3 to the handle unit 2. That is, the transducer unit 3 is attached to the unit body 2 by the transducer attachment part 6.

The rotary knob 9 forms an annular shape and is provided to be rotatable in relation to the unit body 2. The rotary knob 9 rotates the probe 4 and jaw 14 (sheath 10) about an axis of the probe 4 (sheath 10) within a predetermined angular range manually by an operator. In this manner, a direction of grasping a living tissue can be freely set.

In addition, a handle part which is configured by the fixed handle 7 and the movable handle 8 are provided at a lower part of the unit body 2. The fixed handle 7 is formed integrally with the unit body 2, and functions as a grip to be grasped by a hand. The movable handle 8 is provided to be pivotable on the unit body 2 behind the fixed handle 7. The movable handle 8 makes the jaw 14 to operate to open/close through a movement mechanism not shown. That is, the jaw 14 is pivoted in relation to a probe tip end 4b by pivoting the movable handle 8 in relation to the fixed handle 7. In this manner, a living tissue can be grasped between the jaw 14 and the treatment part 5.

Further, the body unit 2 is provided with the switch 11 as a treatment instruction part (first instruction part) to be applied with ultrasonic vibration by the probe 4 (at an upper part 9 of the fixed handle 7). Although details will be described later, as the switch 11 is pressed down, drive energy suitable for treating a living tissue is supplied from the power supply unit 12 to the transducer unit 3. The present embodiment is configured in a manner that the switch 11 of the treatment instruction part is integrally provided on the unit body. However, the embodiment is not limited to this configuration but a foot switch may be provided optionally.

The handle unit 2 according to the present embodiment is configured to comprise the fixed handle 7, movable handle 8, rotary knob 9, and jaw 14. However, these components are not mandatory. That is, insofar as a treatment needs not be performed grasping a living tissue, the fixed handle 7, movable handle 8, or jaw 14 needs not be provided. If the probe 4 needs not be rotated about an axis thereof, the rotary knob 9 needs not be provided.

The power supply unit 12 comprises: a display part 31 which displays a variety of information set up; an operation panel 32 comprising switches for inputting various settings and operation instructions and/or a touch panel provided on a screen; a power supply part 33 which generates a variety of energy (currents) for treating a living tissue and for performing a destruction treatment by the probe 4 described later; a main switch (SW) 34 for turning on/off the power supply unit 12; a destruction SW 35 as a destruction treatment instruction part (second instruction part) for electrically conducting a destruction current to the transducer unit 3 described later; and a controller 36 which controls the respective componential parts.

The power supply part 33 comprises: a treatment power supply part 37 as a first energy generator which generates treatment energy (a treatment current) supplied to the transducer unit 3 (ultrasonic vibration element 21), in order to generate ultrasonic vibration suitable for treating a living tissue; and a destruction power supply part 38 as a second energy generator which generates destruction energy (a destruction current) supplied to the transducer unit 3 (ultrasonic-vibration element 21), in order to generate ultrasonic vibration suitable for destroying the probe 4 and/or the treatment part 5.

If the treatment power supply part 37 can generate a destruction current, the power supply part 38 may substitute for the treatment power supply part 37, and the destruction power supply part 38 needs not always be provided. The destruction mentioned herein is to make at least the treatment part 5 unable to properly treat a living tissue normally. For example, a part of the probe 4 including the treatment part 5 is cracked to make a state that ultrasonic vibration is not properly transmitted.

Further, the destruction SW 35 as a destruction-treatment instruction part, which is provided on the power supply unit 12, may alternatively provided on the handle unit 2. If the destruction SW 35 is provided on the handle unit 2, the SW 35 is desirably provided at a position where an operator cannot operate the SW 35 with the handle unit 2 grasped.

In such a configuration, the handle unit 2 sends a trigger signal to the power supply part 12 upon an ON operation of pressing down the switch 11 when the treatment part 5 is brought into contact with a treatment target portion or when a treatment target portion is pinched. The treatment power supply part 37 of the power supply unit 12 supplies treatment energy (a treatment current) to the ultrasonic vibration element (for example, a piezoelectric element) 21, in response to the trigger signal, and drives the ultrasonic vibration element 21. The handle unit 2 applies generated ultrasonic vibration to the treatment part 5 through the probe 4, to perform a desired treatment.

Next, when an OFF operation to return the switch 11 is carried out, a trigger signal is sent to the treatment power supply part 37 of the power supply unit 12, and the ultrasonic vibration element stops driving. The switch 11 may be used not only for ON/OFF control dependent on sending of the trigger signal but also for presence or absence of supply from a drive power supply dependent on conduction/non-conduction of a switch contact (momentary) in a current circuit (closed loop circuit) including the ultrasonic vibration element.

Figure 3:
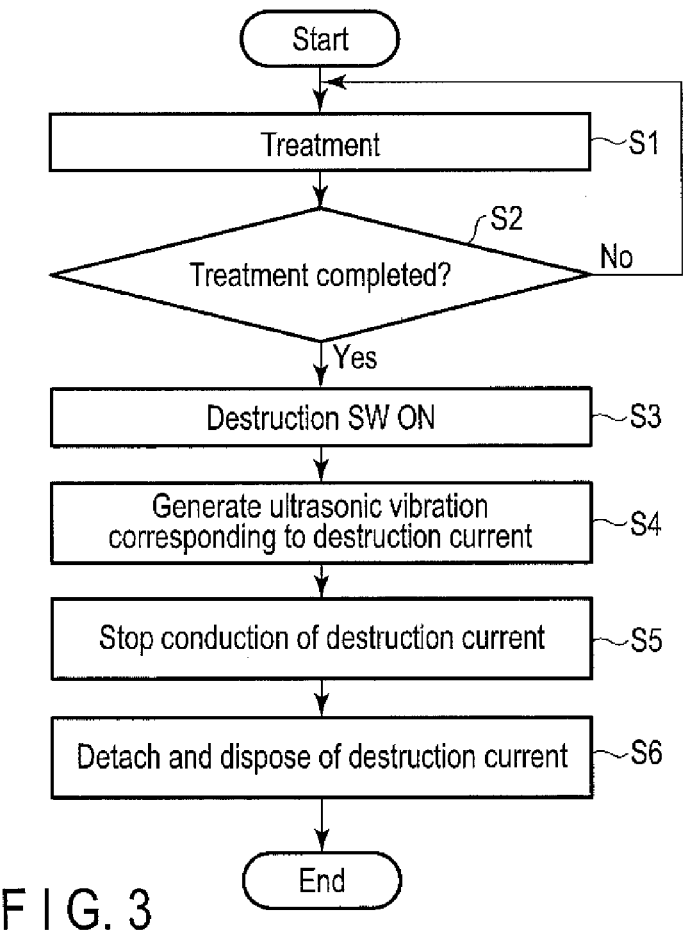
FIG. 3 is a flowchart for explaining a destruction procedure of the probe 4 according to the first embodiment.

Next, with reference to FIG. 2 and FIG. 3, a description will be made of destruction of the probe 4 including the treatment part 5 using the destruction current in the ultrasonic treatment system according to the present embodiment. FIG. 2 shows a waveform A of treatment energy (a treatment current) which the treatment power supply part 37 (first energy generator) generates in order to generate ultrasonic vibration suitable for treating a living tissue, and a waveform B of destruction energy (a destruction current) which is generated by the probe 4 and/or the destruction power supply part 38 (a second energy generator) to destroy the treatment part 5. FIG. 3 is a flowchart for explaining a destruction procedure for the probe 4 and/or the treatment part 5.

The destruction power supply part 38 outputs a destruction current B for destroying the probe 4 by the ON operation of the switch 35 provided on the power supply unit 12. As described above, the destruction switch 35 may be provided on the handle unit 2.

The destruction current B shown in FIG. 2 is a current supplied to the transducer unit 3 (ultrasonic vibration element 21), in order to destroy the probe 4 which the destruction power supply part 38 outputs. The destruction current B is a current value which is, for example, two to three times greater than a current value A generated by the treatment power supply part 37 to generate ultrasonic vibration suitable for treating a living tissue. That is, the current value of the destruction current B is greater than the current value of the treatment current A. By supplying the transducer unit 3 with such a destruction current B, the ultrasonic vibration element 3 generates greater ultrasonic vibration than the treatment current A. In other words, when the treatment current A is supplied to the transducer unit 3, the probe 4 generates ultrasonic vibration with a first amplitude. When the destruction current B is supplied to the transducer unit 3, the probe 4 generates ultrasonic vibration with a second amplitude greater than the first amplitude. The second amplitude is two to three times greater than the first amplitude. Thus, when the treatment current A is supplied to the transducer unit 3, the probe 4 generates greater ultrasonic vibration, compared with when the transducer unit 3 is supplied with the destruction current B. As a result, the probe 4 and/or the treatment part 5 are cracked. In other words, the destruction power supply part 38 (second energy generator) supplies the transducer unit 3 with the destruction current B to an extent (level) that cracks the probe 4 and/or the treatment part 5.

Thus, according to the present embodiment, the probe 4 and/or the treatment part 5 is cracked in a manner that the amplitude of the ultrasonic vibration generated by the transducer unit 3 (ultrasonic vibration element 21) is increased to be greater than that during a treatment.

The current value of the destruction current B is supplied to the transducer unit 3, and is therefore set to a value in consideration of electrical properties, such as current and voltage endurances of the transducer unit 3.

The destruction treatment of the probe 4 will now be described with reference to FIG. 3.

Firstly, a treatment is performed by ultrasonic vibration in accordance with an ordinary procedure (Step S1). Next, the operator determines whether the treatment has been completed or not (Step S2). The completion of a treatment mentioned herein means when a session of surgical operation is perfectly finished or when the treatment instrument configured by the handle unit 2 and the transducer unit 3 becomes unused again during a surgical operation. If the treatment is determined to have been completed in Step 2 (YES), an operation staff carries out an ON operation of the destruction switch 35 without touching the probe 4 (Step S3). By the ON operation, the controller 36 drives the destruction power supply part 38 to output the destruction current (Step S4). The outputted destruction current is supplied to the transducer unit 3, and the ultrasonic-vibration element 21 generates ultrasonic vibration corresponding to the destruction current A. Since the generated ultrasonic vibration is transmitted to the probe 4, the probe 4 and/or the treatment part 5 is cracked.

When a preset time elapses since electrically conducting the destruction current, current output from the destruction power supply part 38 stops (Step S5). Whether cracking occurs or not may be detected depending on a change of the current value of the electrically conducted destruction current. Then, the connector 39 is removed from the power supply unit 12. Further, the transducer unit 3 is detached from the transducer attachment part 6, and the handle unit 2 is put into a predetermined disposal container (Step S6).

As described above, after a treatment on a living tissue is completed, a destruction current is supplied to the transducer unit 3 from the destruction power supply part 38, and the transducer unit 3 is made ultrasonically vibrate in correspondence with the destruction current. As a result, the probe 4 and/or the treatment part 5 is cracked. Therefore, reuse can be prevented securely.

Modification of First Embodiment

FIG. 4 is a block diagram showing a configuration of an ultrasonic treatment system according to a modification of the first embodiment. In the present modification, the power supply unit 12 further comprises a lock unit 40. The other features are the same as those of the configuration of the first embodiment described above, and descriptions thereof will be omitted.

The lock unit 40 has a function to lock connection when the power cable 13 is connected to the power supply unit 12 through the connector 39. Also, the lock unit 40 has a function to release the locked state in a manner that the power cable 13 is detachable from the power supply unit 12 when the destruction switch 35 is pressed.

A specific operation of the lock unit 40 will be described.

In order to treat a living tissue, the power cable 13 is connected to the power supply unit 12 through the connector 39. At this time, the lock unit 40 is set in a locked state so that the power cable 13 may not be detached from the power supply unit 12. That is, the lock unit 40 operates so as not to release connection between the power cable 13 and the power supply unit 12 before a treatment is completed.

When the treatment is completed, an operation staff carries out an ON operation of the destruction switch 35 without touching the probe 4. The destruction current is outputted from the destruction power supply part 38 by the ON operation. At the same time, the lock unit 40 releases the locked state between the power cable 13 and the power supply unit 12. That is, the power cable 13 becomes detachable from the power supply unit 12.

Thus, when the power cable 13 is connected to the power supply unit 12, the lock unit 40 sets a locked state in association with the operation of connection, in which the connection between the power cable 13 and the power supply unit 12 cannot be released. Further when the destruction switch 35 is pressed down, the connection between the power cable 13 and the power supply unit 12 is set in an unlocked state of releasing the connection, in association with the operation. In other words, when the power cable 13 and the power supply unit 12 is connected to each other, the lock unit 40 locks the connection therebetween so as not to be released before a destruction current is supplied. When the destruction current is supplied, the lock unit 40 then operates to release the connection between the power cable 13 and the power supply unit 12.

As described above, since the lock unit 40 is provided in the present modification, the connection between the power cable 13 and the power supply unit 12 is prevented from being released before the destruction switch 35 is pressed. In this manner, forgetting to press the destruction switch 35 can be prevented, and reuse of the probe 4 can also be prevented more securely.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment system for use with a living tissue, the ultrasonic treatment system comprising:
    a transducer including an ultrasonic transducer configured to generate ultrasonic vibrations;
    a handle including a probe configured to transmit the ultrasonic vibrations generated by the transducer;
    a treatment power supply configured to generate a treatment enemy to ultrasonically vibrate the probe with a first amplitude; the treatment energy being adapted to treat the living tissue;
    a destruction power supply configured to generate a destruction energy to ultrasonically vibrate the probe with a second amplitude, the destruction energy being configured to destroy the probe such that reuse of the probe is prevented, the second amplitude being greater than the first amplitude;
    a switch configured to generate a first signal in response to a first operation by a user;
    a destruction switch configured to generate a second signal in response to a second operation by the user;
    a controller configured to drive: (i) the treatment power supply based on the first signal, and (ii) the destruction power supply based on the second signal;
    a power supply cable configured to connect: (i) a power supply including the treatment power supply and the destruction power supply, and (ii) the transducer; and
    a lock configured to prevent a connection of the power supply cable to the power supply from being released when the power supply cable is connected to the power supply, the lock being set to: (A) a locked state in which connection between the power supply cable and a power supply is not released, in response to an operation of the power supply cable being connected to the power supply, and (B) an unlocked state in which the connection is released upon receipt of an instruction from the destruction switch.

2. The ultrasonic treatment system of claim 1, wherein the second amplitude has a magnitude of at least two to three times greater than a magnitude of the first amplitude.

3. The ultrasonic treatment system of claim 1, wherein the destruction switch is provided on the handle.

* * * * *